United States Patent [19]

Canavesio et al.

[11] 4,289,143
[45] Sep. 15, 1981

[54] METHOD OF AND APPARATUS FOR AUDIOMETRICALLY DETERMINING THE ACOUSTIC IMPEDANCE OF A HUMAN EAR

[75] Inventors: Franco Canavesio; Rodolfo Ceruti, both of Turin, Italy

[73] Assignee: CSELT Centro Studi e Laboratori Telecomunicazioni S.p.A., Turin, Italy

[21] Appl. No.: 110,801

[22] Filed: Jan. 9, 1980

[30] Foreign Application Priority Data

Jan. 12, 1979 [IT] Italy .............................. 67058 A/79

[51] Int. Cl.³ .............................................. A61B 5/12
[52] U.S. Cl. .................................. 128/746; 179/1 N; 73/585; 73/589
[58] Field of Search ............... 128/746, 647; 179/1 N; 73/585, 589

[56] References Cited

U.S. PATENT DOCUMENTS

| | | | |
|---|---|---|---|
| 3,395,697 | 8/1968 | Mendelson | 179/1 N |
| 3,757,769 | 9/1973 | Arguimbau et al. | 128/746 |
| 3,882,848 | 5/1975 | Klar et al. | 128/746 |
| 3,949,735 | 4/1976 | Klar et al. | 128/746 |
| 4,002,161 | 1/1977 | Klar et al. | 128/746 |
| 4,009,707 | 3/1977 | Ward | 128/746 |
| 4,079,198 | 3/1978 | Bennett | 128/746 |
| 4,237,905 | 12/1980 | Keller et al. | 128/746 |

OTHER PUBLICATIONS

Butenko, L. N. et al., Biomed. Eng., May-Jun. 1976, vol. 10, No. 3, pp. 178-179. (Publ. Jan. 1977).
Gintsburg, B. C., et al., Biomedical Engr., vol. 9, No. 5, pp. 287-289, (Publ: May 1976).

Primary Examiner—Kyle L. Howell
Assistant Examiner—John C. Hanley
Attorney, Agent, or Firm—Karl F. Ross

[57] ABSTRACT

In order to determine the acoustic impedance of a human ear at various static pressures, a probe tightly fitted to the pinna of the ear transmits a short acoustic pulse with a wide frequency spectrum (such as white noise) from an electroacoustic transducer to the ear canal and receives back an acoustic response signal which a microphone converts into an electrical wave. The latter is digitized and transformed into terms of a Fourier series fed to a processor which, on the basis of similar terms stored in a memory and previously obtained with the same probe fitted to two different cylindrical calibrating cavities, derives therefrom the acoustic ear impedance at a particular air pressure. The processor also triggers an electric pulse generator, working into the electroacoustic transducer, and may progressively adjust a generator of static air pressure connected to the probe.

7 Claims, 3 Drawing Figures

METHOD OF AND APPARATUS FOR AUDIOMETRICALLY DETERMINING THE ACOUSTIC IMPEDANCE OF A HUMAN EAR

FIELD OF THE INVENTION

Our present invention relates to a method of audiometrically determining the acoustic impedance of a human ear and to an apparatus for implementing the method.

BACKGROUND OF THE INVENTION

Audiometric tests designed to detect malformations of the inner ear generally involve the measurement of the acoustic impedance at various frequencies in the audible range. Aside from their clinical uses, such measurements are also important in the technical field to facilitate the construction of simulated impedances utilized in checking the performance of intra-aural devices such as hearing aids, stethoscopic headphones and earplugs.

The conventional method of measuring the acoustic impedance of the ear entails the generation of tones of a specific audio frequency, usually 220 or possibly 660 Hz, fed to the ear canal through a suitable probe. Though the same technique could be applied with other frequencies in the range of interest, the switchover from one frequency to the other and the amplitude measurements needed in each instance would require a lengthy procedure and would thus be inconvenient especially for diagnostic purposes.

OBJECTS OF THE INVENTION

An object of our present invention, therefore, is to provide a greatly simplified method of determining the acoustic impedance of the ear over a wide range of audible frequencies.

A related object is to provide a simple apparatus for carrying out this method.

SUMMARY OF THE INVENTION

In accordance with our present invention, a channeled probe is tightly fitted to a first cylindrical calibrating cavity of radius $a_1$ and length $L_1$ which is then placed, via a channel of that probe, under a static air pressure $P_i$. A short acoustic pulse encompassing a wide spectrum of audible frequency, preferably obtained from a generator of white noise, is transmitted to the cavity via a channel of the probe whereupon an acoustic response signal, received back from the cavity via another probe channel, is transformed into an electrical wave which is then converted into terms of a Fourier series representing a first set of amplitude samples $S_{1i}(\omega_x)$ of a plurality of constituent frequencies $f_x = \omega_x/2\pi$. The amplitude samples $S_{1i}(\omega_x)$ are stored in a memory, preferably in digitized form, and the same steps are repeated with the probe fitted to a second cylindrical calibrating cavity of radius $a_2$ and length $L_2$ yielding a second set of amplitude samples $S_{2i}(\omega_x)$ which are also stored. Finally, the probe is fitted in an airtight manner to the pinna of the ear to be tested and the aforedescribed steps of pulse transmission, transformation of the resulting acoustic response signal into an electrical wave and conversion thereof into terms of a Fourier series are again performed to yield a third set of amplitude samples $S_{xi}(\omega_x)$ from which the acoustic impedance $Z_{xi}(\omega_x)$ for the given air pressure $P_i$ and for different frequencies $f_x$ can be calculated on the basis of the stored amplitude samples according to the formula $$Z_{xi}(\omega_x) = \frac{\gamma P_i}{j\pi v a_1^2} \cot \frac{\omega_x L_1}{v} \cdot \frac{\frac{S_{xi}(\omega_x)}{S_{1i}(\omega_x)}\left[\frac{S_{1i}(\omega_x)}{S_{2i}(\omega_x)} - 1\right]}{\frac{a_2^2 \cot \frac{\omega_x L_1}{v}}{a_1^2 \cot \frac{\omega_x L_2}{v}} - 1 - \frac{S_{xi}(\omega_x)}{S_{1i}(\omega_x)}\left[\frac{a_2^2 \cot \frac{\omega_x L_1}{v}}{a_1^2 \cot \frac{\omega_x L_2}{v}} - \frac{S_{1i}(\omega_x)}{S_{2i}(\omega_x)}\right]} \tag{1}$$

where $v$ is the propagation speed of sound in air and $\gamma$ is a fixed parameter, specifically the ratio $c_p/c_V$ ($c_p$ and $c_V$ being the specific heat of the pressure medium at constant pressure and volume, respectively); with air, $\gamma = 1.41$. The operator $j$, of course, stands for $\sqrt{-1}$.

An apparatus for carrying out this method comprises a source of static air pressure communicating with a channel of the probe, an electroacoustic transducer connected to one of its channels, and a microphone connected to another channel thereof. A generator of short electric pulses encompassing a wide spectrum of audio frequencies has an output connected to the transducer while the microphone works into a signal analyzer producing the aforementioned amplitude samples. A memory connectable to the signal analyzer stores the first and second sets of amplitude samples, obtained when the probe is successively fitted in an airtight manner to the two calibrating cavities, both the signal analyzer and the memory being connected to a processor operating in accordance with equation (1) to provide the desired impedance value $Z_{xi}(\omega_x)$.

The source of air pressure is advantageously adjustable to provide a plurality of different static pressures $P_i$, above and below atmospheric pressure, for which the acoustic impedance may be individually determined.

BRIEF DESCRIPTION OF THE DRAWING

The above and other features of our present invention will now be described in detail with reference to the accompanying drawing in which.

SPECIFIC DESCRIPTION

Figure 1:
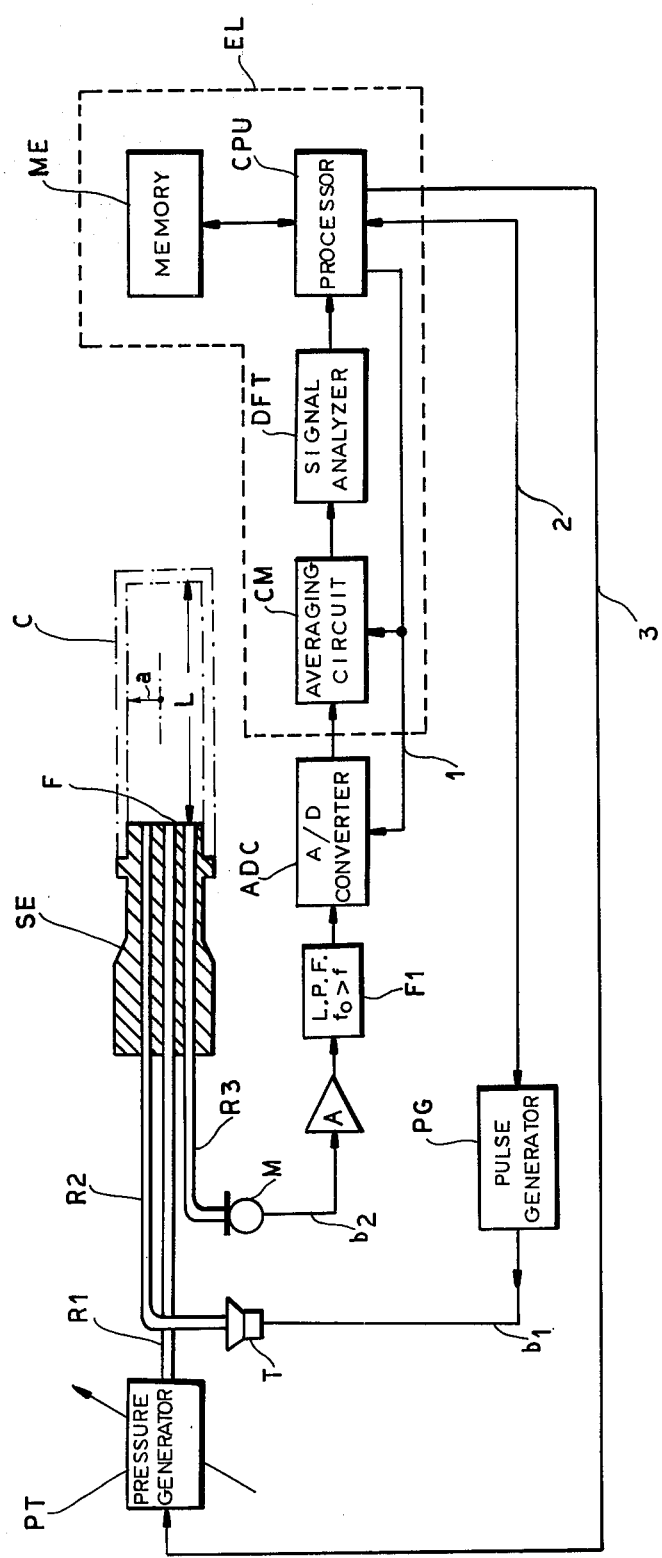
FIG. 1 is a block diagram of an apparatus for determining an acoustic ear impedance pursuant to our invention.

In FIG. 1 we have shown a probe SE which can be hermetically fitted to the outer ear of a person as well as to several cylindrical calibrating cavities C of different radii $a$ and lengths $L$ as indicated in phantom lines. Probe SE is shown to have three channels terminating flush at a transverse face F, these channels being extensions of conduits R1, R2 and R3 respectively connected to a pressure generator PT, an electroacoustic transducer T shown as a loudspeaker, and a microphone M. An electrical pulse generator PG has an output lead $b_1$ extending to transducer T and emits short pulses Q of white noise, shown in FIG. 2, of width $\Delta t \leq \frac{1}{2} f_o$ with $f_o$ representing the upper limit of the band of audio frequencies in which the acoustic impedance of the ear is to be ascertained.

Figure 2:
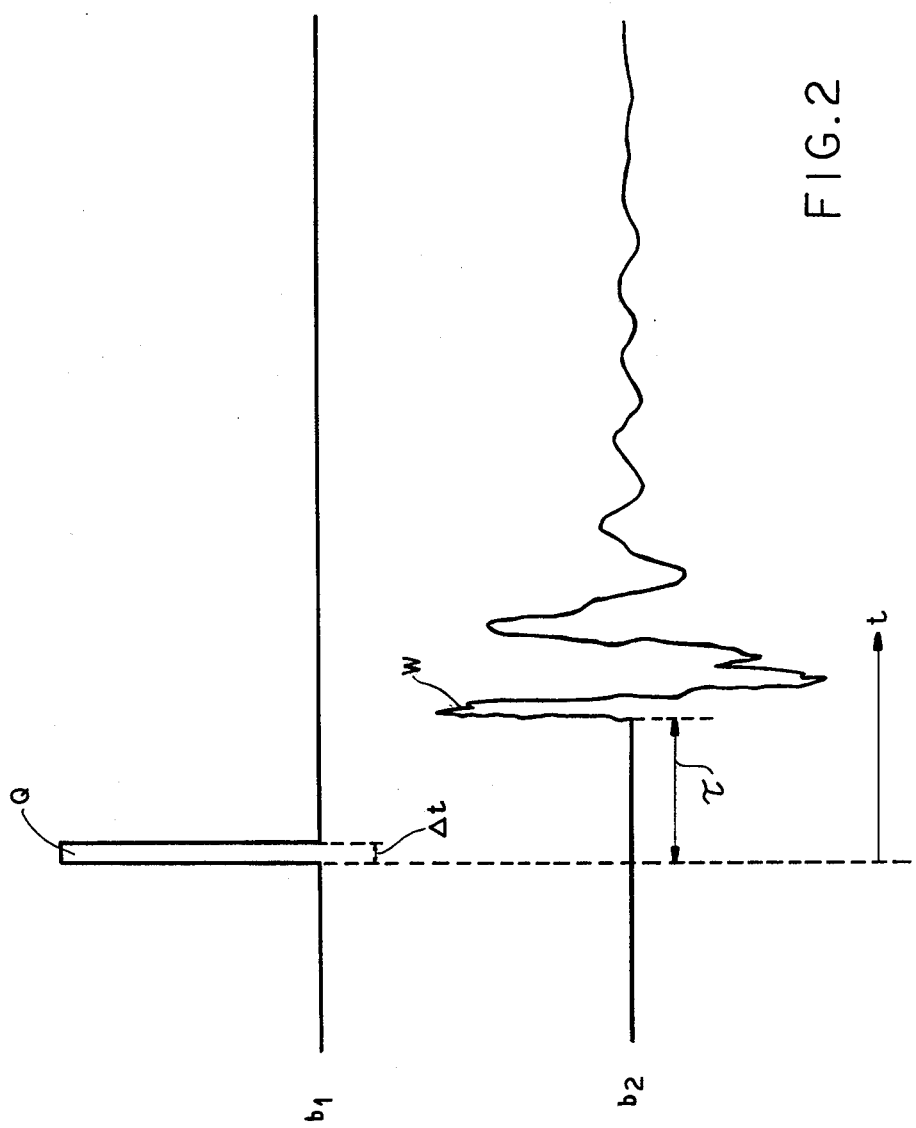
FIG. 2 is a set of graphs relating to the operation of the apparatus of FIG. 1.

Microphone M feeds, via an output lead $b_2$ and an amplifier A, a low-pass filter FI with cutoff frequency $f_o$; filter FI may be omitted where at least one of the two transducers T and M operates with an inherent cutoff frequency of the desired value. Such transducers are commercially available. An electrical wave W appearing on lead $b_2$, as illustrated in FIG. 2, is delivered after amplification and filtering to an analog/digital converter ADC working into an evaluator EL. The leading edge of wave W is separated from that of the coresponding excitation pulse Q by a time interval $\tau$ which is due to the transit time of the sound waves passing through conduits R2 and R3, this transit time being fixed for a given apparatus and being thus readily taken into account in the processing of the signals from converter ADC by evaluator EL. The sampling rate of the converter is at least equal to and preferably greater than $2f_o$.

The evaluator comprises a circuit CM which, in order to increase the signal-to-noise ratio, averages homologous digitized samples taken from signal waves W that are excited at the same pressure $P_i$ by consecutive pulses Q. Circuit CM feeds a signal analyzer DFT which, preferably implementing the algorithm known as Fast Fourier Transform (FFT), derives from these signal samples a series of Fourier terms representing amplitude samples of the most significant constituent frequencies of that wave. A processor CPU coacts with signal analyzer DFT and with a memory ME for the purpose of storing therein the amplitude samples $S_{1i}(\omega_x)$ and $S_{2i}(\omega_x)$ obtained during calibration when the probe SE is coupled with respective cavities C of predetermined radii $a_1$, $a_2$ and lengths $L_1$, $L_2$. The processor includes a timer which, via lines 1 and 2, correlates the operation of circuits ADC and CM with that of pulse generator PG. Line 2 is a bidirectional connection over which the pulse generator PG sends back a confirmation signal after having been triggered by the processor CPU into the emission of each excitation pulse Q. A line 3 extending from the processor to the adjustable pressure generator PT enables the static pressure in conduit R1 to be progressively modified between groups of excitation pulses Q.

With filter FI cutting off all frequencies in wave W whose half-cycles are less than the duration of an excitation pulse Q, as noted above, the spectrum of these pulses within the operating band of evaluator EL is sufficiently devoid of transients for satisfactory digital processing.

Although conduit R1 originating at pressure generator PT is shown connected to a separate channel of probe SE, it could also be merged with conduit R2 or R3 in order to eliminate one such channel.

It can be shown, on the basis of available literature, that an unknown acoustic impedance $Z_x(\omega)$ can be determined from an associated transfer function $S_x(\omega)$, with the aid of corresponding transfer functions $S_1(\omega)$ and $S_2(\omega)$ obtained with calibrating cavities of volumes $V_1$ and $V_2$ at a given pulsatance $\omega$, according to the formula $$Z_x(\omega) = \frac{\gamma P_o}{j\omega v_1} \left( \frac{\frac{S_x(\omega)}{S_1(\omega)}\left[\frac{S_1(\omega)}{S_2(\omega)} - 1\right]}{\left[\frac{v_2}{v_1} - 1\right] - \frac{S_x(\omega)}{S_1(\omega)}\left[\frac{v_2}{v_1} - \frac{S_1(\omega)}{S_2(\omega)}\right]} \right) \quad (2)$$

where $P_o$ is atmospheric pressure and $\gamma$ and j have the same significance as in equation (1). Equation (2) is applicable to conventional audiometric methods as discussed above, using sinusoidal test signals, but does not take into account the geometric shape of the calibrating cavities and is therefore not suitable for measurements carried out over a wide frequency spectrum. By modifying that equation, in light of the known properties of rigid cylindrical cavities as taught for example in a book entitled ACOUSTICS by L. Beranek, published 1954 by McGraw-Hill Co. (see particularly page 128), we have arrived at equation (1) underlying the operation of processor CPU. The results of that operation, i.e. the magnitudes of impedances $Z_{xi}(\omega_x)$ for different pulsatances $\omega_x = 2\pi f_x$ and possibly different static pressures $P_i$, can be fed to a visual indicator and/or registered on a suitable recording medium.

Figure 3:
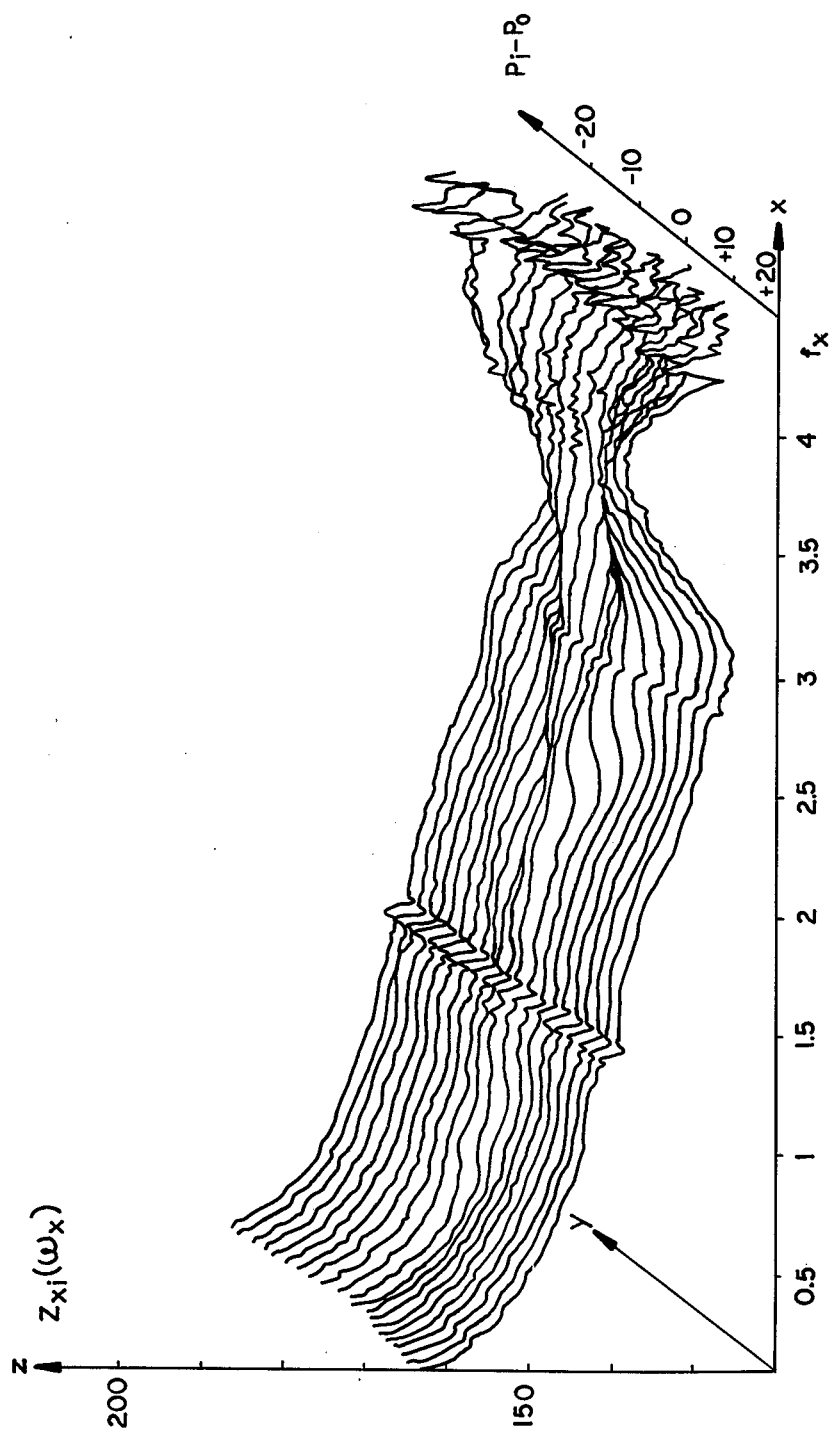
FIG. 3 is an axonometric view of a family of curves representing the acoustic impedance $Z_{xi}(\omega_x)$ for different air pressures $P_i$ and frequencies $f_x$.

FIG. 3 illustrates a family of curves representing acoustic impedance as a function of audible frequencies $f_x$ (in KHz) and pressure differences $P_i - P_o$ (in cm of water column) respectively plotted on axes x and y of a Cartesian coordinate system, with impedance $Z_{xi}(\omega_x)$ plotted along the z axis and measured in dB with reference to a unit impedance of $1 \text{N·sec/m}^5$ (N being force in Newtons). Each of these curves is derived from a single excitation pulse P, or from a group of spaced-apart excitation pulses whose response signals are sampled coherently by A/D converter ADC under the control of processor CPU.

We claim:

1. A method of determining the acoustic impedance of a human ear, comprising the steps of:
    (a) tightly fitting a channeled probe to a first cylindrical calibrating cavity of radius $a_1$ and a length $L_1$;
    (b) placing said cavity, via a channel of said probe, under a predetermined static air pressure $P_i$;
    (c) transmitting to said cavity, via a channel of said probe, a short acoustic pulse encompassing a wide spectrum of audible frequencies;
    (d) receiving back from said cavity, via another channel of said probe, an acoustic response signal and transforming an electrical wave converted into terms of a Fourier series representing a first set of amplitude samples $S_{1i}(\omega_x)$ of a plurality of constituent frequencies $f_x = \omega_x/2\pi$;
    (e) storing the amplitude samples $S_{1i}(\omega_x)$ obtained in step (d);
    (f) repeating steps (a) through (e) with said probe fitted to a second cylindrical calibrating cavity of radius $a_2$ and length $L_2$, thereby obtaining and storing a second set of amplitude samples $S_{2i}(\omega_x)$;
    (g) repeating steps (a) through (d) with said probe fitted to the pinna of a human ear to be tested, thereby detecting a third set of amplitude samples $S_{xi}(\omega_x)$; and
    (h) calculating the acoustic impedance $Z_{xi}(\omega_x)$ for said air pressure $P_i$ and for different frequencies $f_x$ from the corresponding stored amplitude samples $S_{1i}(\omega_x)$, $S_{2i}(\omega_x)$, the corresponding detected amplitude samples $S_{xi}(\omega_x)$, the propagation speed v of sound in air, and a fixed parameter $\gamma$, according to the following formula:

$$Z_{xi}(\omega_x) = \frac{\gamma p_i}{j\pi v a_1^3} \cot\frac{\omega_x L_1}{v} \cdot \frac{\frac{S_{xi}(\omega_x)}{S_{1i}(\omega_x)}\left[\frac{S_{1i}(\omega_x)}{S_{2i}(\omega_x)} - 1\right]}{\frac{a_2^3 \cot\frac{\omega_x L_1}{v}}{a_1^3 \cot\frac{\omega_x L_2}{v}} - 1 - \frac{S_{xi}(\omega_x)}{S_{1i}(\omega_x)}\left[\frac{a_2^3 \cot\frac{\omega_x L_1}{v}}{a_1^3 \cot\frac{\omega_x L_2}{v}} - \frac{S_{1i}(\omega_x)}{S_{2i}(\omega_x)}\right]}$$

2. A method as defined in claim 1, comprising the further step of varying said static air pressure $P_i$, thereby obtaining a series of different values of said acoustic impedance $Z_{xi}(\omega_x)$.

3. An apparatus for determining impedance of a human ear, comprising:
a probe adapted to be hermetically secured to the pinna of a human ear and provided with a plurality of throughgoing channels;
a source of static air pressure communicating with a channel of said probe;
an electroacoustic transducer connected to one of said channels;
a microphone connected to another of said channels;
a generator of short electric pulses encompassing a wide spectrum of audio frequencies, said generator having an output connected to said transducer;
signal-analyzing means connected to said microphone for receiving an electrical wave emitted thereby in response to a pulse fed from said generator to said transducer and deriving therefrom, with a given air pressure $P_i$ from said source, a first set of amplitude samples $S_{1i}(\omega_x)$ of a plurality of constituent frequencies $f_x = \omega_x/2\pi$ upon a fitting of said probe to a first cylindrical calibrating cavity of radius $a_1$ and length $L_1$, a second set of amplitude samples $S_{2i}(\omega_x)$ of the same constituent frequencies $f_x$ upon a fitting of said probe to a second cylindrical calibrating cavity of radius $a_2$ and length $L_2$, and a third set of amplitude samples $S_{xi}(\omega_x)$ upon a fitting of said probe to an ear to be tested;
memory means connectable to said signal-analyzing means for storing said first and second sets of amplitude samples; and
processing means connected to said analyzing means and to said memory means for calculating the acoustic impedance $Z_{xi}(\omega_x)$ for said air pressure $P_i$ and for different frequencies $f_x$ from the corresponding amplitude samples $S_{1i}(\omega_x)$, $S_{2i}(\omega_x)$ and $S_{xi}(\omega_x)$, the propagation speed v of sound in air, and a fixed parameter $\gamma$, according to the following formula:

$$Z_{xi}(\omega_x) = \frac{\gamma p_i}{j\pi v a_1^3} \cot\frac{\omega_x L_1}{v} \cdot \frac{\frac{S_{xi}(\omega_x)}{S_{1i}(\omega_x)}\left[\frac{S_{1i}(\omega_x)}{S_{2i}(\omega_x)} - 1\right]}{\frac{a_2^3 \cot\frac{\omega_x L_1}{v}}{a_1^3 \cot\frac{\omega_x L_2}{v}} - 1 - \frac{S_{xi}(\omega_x)}{S_{1i}(\omega_x)}\left[\frac{a_2^3 \cot\frac{\omega_x L_1}{v}}{a_1^3 \cot\frac{\omega_x L_2}{v}} - \frac{S_{1i}(\omega_x)}{S_{2i}(\omega_x)}\right]}$$

4. An apparatus as defined in claim 3 wherein said source is adjustable, said processing means having output connections to said source and to said generator for repetitively triggering the latter with different air pressures $P_i$.

5. An apparatus as defined in claim 3 or 4, further comprising filter means inserted between said microphone and said signal-analyzing means for suppressing frequencies in said electrical wave whose half-cycles are less than the duration of a pulse emitted by said generator.

6. An apparatus as defined in claim 3 or 4, further comprising analog/digital conversion means inserted between said microphone and said signal-analyzing means.

7. An apparatus as defined in claim 6, further comprising digital amplitude-averaging means between said conversion means and said signal-analyzing means.

* * * * *